(12) United States Patent
Park (10) Patent No.: US 11,890,370 B2
(45) Date of Patent: Feb. 6, 2024

(54) ULTRASOUND-INDUCED DRUG DELIVERY SYSTEM USING DRUG CARRIER COMPRISING NANOBUBBLES AND DRUG

(71) Applicants: SAHMYOOK UNIVERSITY INDUSTRY-ACADEMIC COOPERATION FOUNDATION, Seoul (KR); N to B Co., Ltd, Seoul (KR)

(72) Inventor: Myoung Hwan Park, Gyeonggi-do (KR)

(73) Assignees: SAHMYOOK UNIVERSITY INDUSTRY-ACADEMIC COOPERATION FOUNDATION, Seoul (KR); N TO B CO., LTD., Seoul (KR)

( * ) Notice: Subject to any disclaimer, the term of this patent is extended or adjusted under 35 U.S.C. 154(b) by 0 days.

(21) Appl. No.: 17/049,468

(22) PCT Filed: Sep. 20, 2019

(86) PCT No.: PCT/KR2019/012217
§ 371 (c)(1),
(2) Date: Oct. 21, 2020

(87) PCT Pub. No.: WO2020/060275
PCT Pub. Date: Mar. 26, 2020

(65) Prior Publication Data
US 2021/0259953 A1 Aug. 26, 2021

(30) Foreign Application Priority Data
Sep. 21, 2018 (KR) .................. 10-2018-0113896

(51) Int. Cl.
*A61K 9/00* (2006.01)
*A61K 8/06* (2006.01)
*A61K 8/11* (2006.01)
*A61K 9/107* (2006.01)
*A61K 9/51* (2006.01)
*A61K 45/06* (2006.01)
*B82Y 5/00* (2011.01)

(52) U.S. Cl.
CPC ............ *A61K 9/0009* (2013.01); *A61K 8/06* (2013.01); *A61K 8/11* (2013.01); *A61K 9/107* (2013.01); *A61K 9/5192* (2013.01); *A61K 45/06* (2013.01); *A61K 2800/10* (2013.01); *A61K 2800/413* (2013.01); *B82Y 5/00* (2013.01)

(58) Field of Classification Search
CPC .. A61K 31/538; A61K 9/0019; A61K 31/704; A61K 45/06; A61K 47/44; A61K 9/0053; A61K 9/0009; A61K 9/5192; A61K 9/107; A61K 9/5089; A61K 41/0028; A61K 8/06; A61K 8/11; A61K 2800/413; A61K 2800/10; B82Y 5/00
See application file for complete search history.

(56) References Cited

U.S. PATENT DOCUMENTS

| 5,919,434 | A | 7/1999 | Dugstad et al. |
| 10,478,788 | B2 | 11/2019 | Jung et al. |
| 2004/0131547 | A1* | 7/2004 | Balinov ............ A61K 41/0028 424/9.51 |
| 2006/0284325 | A1* | 12/2006 | Kohama ............ B01F 3/04262 261/122.1 |
| 2012/0109045 | A1* | 5/2012 | Wrenn ................ A61K 9/0009 604/22 |
| 2012/0121516 | A1 | 5/2012 | Tabeling et al. |
| 2017/0259219 | A1* | 9/2017 | Russell ................ B01F 5/0465 |

FOREIGN PATENT DOCUMENTS

| CN | 104096245 A | 10/2014 |
| CN | 104755108 A | 7/2015 |
| JP | 2010163393 A | 7/2010 |
| KR | 1019960704622 A | 9/1996 |
| KR | 20130136910 A | 12/2013 |
| KR | 1020140018150 A | 2/2014 |
| KR | 101487088 B1 | 1/2015 |
| KR | 101595795 B1 | 2/2016 |

(Continued)

OTHER PUBLICATIONS

Wang, Ye, et al., "Preparation of nanobubbles for ultrasound imaging and intracelluar drug delivery," International Journal of Pharmaceutics, 384 (2010) pp. 148-153.
Fabiilli, M., et al. "Delivery of Chlorambucil Using an Acoustically-TriggeredPerfluoropentane Emulsion" Ultrasound in Med. & Biol., vol. 36, No. 8, pp. 1364-1375, 2010.
Hwang, T., et al.,"Development and Evaluation of Perfluorocarbon Nanobubbles for Apomorphine Delivery", Journal of Pharmaceutical Sciences, vol. 98, No. 10, Oct. 2009 3735-33747.
Mograo, J. "Modulation of Dendritic Cells by Nanotechnology-Based Immunotherapeutic Strategies", Journal of Biomedical Nanotechnology, Vo. 12, 405-434, 2016.

(Continued)

*Primary Examiner* — Doan T Phan
(74) *Attorney, Agent, or Firm* — CANTOR COLBURN LLP (57) ABSTRACT

An ultrasound-induced drug delivery system is described, using a drug carrier containing a plurality of nanobubbles and a high concentration of a drug in one microcapsule, and a method for preparing the drug delivery system, by generating the nanobubbles in an oil into which the drug is dissolved using a nanobubble generator, and then microencapsulating them. The drug delivery system has an effect of maximizing a drug delivery efficiency as the nanobubbles collapse or aggregate when the ultrasound is applied to the drug delivery system. Since the drug delivery system contains a plurality of nanobubbles within the microcapsules, it can also be used as a contrast agent, or can be used to simultaneously perform in vivo diagnosis and treatment.

6 Claims, 4 Drawing Sheets

(56) References Cited

FOREIGN PATENT DOCUMENTS

| | | |
|---|---|---|
| KR | 20160120687 A | 10/2016 |
| KR | 20200141326 A | 12/2020 |

OTHER PUBLICATIONS

Translated International Search Report for PCT/KR2019/012217, International Filing Date Sep. 20, 2019, dated Jan. 3, 2020, 3 pages.
Translated Written Opinion for PCT/KR2019/012217, International Filing Date Sep. 20, 2019, dated Jan. 3, 2020, 5 pages.

* cited by examiner

ULTRASOUND-INDUCED DRUG DELIVERY SYSTEM USING DRUG CARRIER COMPRISING NANOBUBBLES AND DRUG

CROSS REFERENCE TO RELATED APPLICATIONS

This application is a National Stage application of PCT/KR2019/012217, filed Sep. 20, 2019, which claims the benefit of Korean Application No. 10-2018-0113896, filed Sep. 21, 2018, both of which are incorporated by reference in their entirety herein.

TECHNICAL FIELD

The present invention relates to an ultrasound-induced drug delivery system using a drug carrier containing a plurality of nanobubbles and a high concentration of a drug in one microcapsule, and specifically is directed to a method for preparing a drug delivery system having a high concentration of a drug and a plurality of nanobubbles encapsulated therein, by generating the nanobubbles in an oil into which the drug is dissolved using a nanobubble generator, and then microencapsulating them; and an ultrasound-induced drug delivery system using the same.

BACKGROUND OF THE INVENTION

A drug delivery system is aimed to maximize treatment efficacy and effect by selectively delivering a drug to a target site and optimizing an effective blood concentration according to a disease for a long time, and to minimize a side effect of the drug.

A nano drug delivery system, which is most of these drug delivery systems, can be prepared by various methods. The nano drug delivery system obtained by a representative preparation method may include nanoparticles obtained by using a self-emulsifying diffusion method, nanoparticles obtained by a micelle formation using a block copolymer, nanoparticles obtained by using a magnetism, nanoparticles obtained by a complex reaction of an ionic polymer, and the likes.

The nanoparticles are delivered into a human body through various routes such as an injection, an oral, and a skin. In this case, distribution of the drug indicates distribution of the drug that is distinct from other delivery systems and this distribution is varied depending on properties of the nanoparticles.

Further, in order to enhance a target delivery efficiency to these nanoparticles, various studies have been conducted in several fields to maximize the drug delivery such as binding between various target ligands, controlling a release rate of the drug through near-infrared irradiation, and improving penetration ability by an ultrasound, but there is still a need to develop an excellent drug delivery technology for controlling drug release to a target site at an appropriate timing and in an appropriate amount.

SUMMARY OF THE INVENTION

Technical Challenge

A purpose of the present invention is to provide a drug delivery system that contains a plurality of nanobubbles together with a drug in a microcapsule, and can effectively deliver the drug by an ultrasound.

Another purpose of the present invention is to provide a method for preparing a drug delivery system that is easily dispersed in an aqueous solution, by generating nanobubbles in an oil into which a fat-soluble drug that is difficult to disperse in water is dissolved, using a nanobubble generator, and then microencapsulating an oil (nanobubble solution) containing the fat-soluble drug and the nanobubbles.

However, the technical challenge to be achieved by the present invention is not limited to the above-mentioned challenges, and other challenges that are not mentioned may be clearly understood from the following descriptions by a person who has an ordinary knowledge in the art.

Technical Solution

As an aspect for attaining the above purposes, the present invention first provides a method for preparing a drug delivery system that is easily dispersed in an aqueous solution, by generating nanobubbles in an oil into which a fat-soluble drug that is difficult to disperse in water is dissolved, using a nanobubble generator, and then microencapsulating the oil containing the oil-soluble drug and the nanobubbles. The term "drug delivery system" in this specification may be used interchangeably with a 'microcapsule' or a 'nanobubble microcapsule'.

In the present invention, a nanobubble solution contains nanobubbles having a diameter in the range of 50 nm to 500 nm, for example, in particular, a diameter in the range of 50 nm to less than 200 nm, and the term "bubble" refers to a foam, that is, a bubble pocket present in a liquid. A concentration of the nanobubble solution according to the present invention, that is, the number of nanobubbles present in the nanobubble solution contains the nanobubbles of 500 million/ml, 1 billion/ml to 3 billion/ml or more. These nanobubbles can be stably maintained at a temperature lower than a room temperature for 2 to 6 months or more. If a size of the nanobubbles is larger than the above range, a stability of the nanobubble solution may be remarkably deteriorated due to floating, and the nanobubble solution having the number of nanobubbles lower than the above range may significantly reduce an ultrasound-induced drug delivery efficiency because the number of nanobubbles in a single microcapsule is small.

The method according to the present invention may comprise the steps of:
(a) dissolving a drug in an organic solvent, and then mixing it with an oil to prepare a mixed solution;
(b) removing the organic solvent from the mixed solution;
(c) preparing an oil solution (nanobubble solution) containing both a fat-soluble drug and nanobubbles, by generating the nanobubbles in the mixed solution from which the organic solvent has been removed, or by preparing an oil containing the drug and an oil containing the nanobubbles, respectively, and then mixing them; and
(d) mixing the nanobubble solution in an aqueous solution containing a surfactant.

According to the present invention, the drug delivery system may be characterized by being dispersed in an aqueous solution in the form of an emulsion.

In the step (c), a mixing ratio of the oil containing the drug and the oil containing the nanobubbles is not particularly limited, and the nanobubble solution of the present invention can be prepared by mixing those oils in an appropriate ratio according to the purpose of a person skilled in the art.

Further, according to the present invention, the step (d) may be to prepare a drug delivery system in the form of a microcapsule having both the drug and the nanobubbles encapsulated therein by passing the oil (nanobubble solution) containing the drug and nanobubbles through a membrane in an aqueous solution containing a surfactant. As an example, the drug delivery system having both the drug and the nanobubbles encapsulated therein may be prepared using an emulsion generator (IMK-40, MC Tech, etc.).

In particular, the drug may be prepared as a drug delivery system in the form of microcapsules by encapsulating the drug with the nanobubbles in the form contained in an oil.

According to the present invention, the drug may be a fat-soluble drug, and may all include a drug having an affinity for a lipid, a drug having a stronger affinity for the lipid or a lipoid than water, a drug having an affinity for a non-polar fluid, and a drug having a functional group capable of binding for the lipid or the lipoid. In addition, the drug is not particularly limited to the above types, and may all include a chemical drug, a protein drug, a peptide drug, a nucleic acid molecule for gene therapy, nanoparticles, an iodide contrast agent, a gadolinium contrast agent, a barium contrast agent, a contrast material such as a fluorescent particle and a magnetic particle, an active ingredient of (functional) cosmetics, or a cosmetically used active ingredient. For example, the active ingredient of (functional) cosmetics or the cosmetically used active ingredient may include niacinamide, arbutin, *Atractylodes macrocephala* Koidzumi oil, 4-en-butylresorcinol, and ethylascorbyl ether, which exhibit a whitening effect; adenosine, asiaticoside, retinol, and retinyl palmitate, which exhibit an anti-wrinkle effect; and cosmetic ingredients that exhibit an antioxidant effect or a UV protection effect, in addition to allantoin, aloe vera extract, azulene, and centella asiatica extract, which exhibit an anti-inflammatory effect, but are not particularly limited thereto.

The fat-soluble drug that can be used in the present invention may include, for example, an anticancer drug, a therapeutic agent for a (degenerative) brain disease, an anti-inflammatory drug, an analgesic, an antiarthritic, an antispasmodic, an antidepressant, an antipsychotic drug, a tranquilizer, an anti-anxiety drug, a drug antagonist, an anti-Parkins disease drug, a cholinergic agonist, an antiangiogenic drug, an immunosuppressant, an antiviral drug, an antibiotic, an appetite suppressant, a pain reliever, an anticholinergic drug, an antihistamine, an antimigraine drug, a hormone drug, a coronary vascular, cerebrovascular or peripheral vasodilator, a contraceptive pill, an antithrombotic agent, a diuretic, an antihypertensive agent, a therapeutic agent for a cardiovascular disease, a cosmetic ingredient (e.g., an anti-wrinkle agent, a skin aging inhibitor and a skin whitening agent), and the like, but are not limited thereto. For example, the fat-soluble drug may be a drug such as doxorubicin, paclitaxel, vincristine, daunorubicin, vinblastine, actinomycin-D, docetaxel, etoposide, teniposide, bisantren, homoharringtonine, Gleevec (STI-571), cisplatin, 5-fluorouracil, adriamycin, methotrexate, busulfan, chlorambucil, cyclophosphamide, melphalan, nitrogen mustard or nitrosourea.

According to the present invention, the organic solvent may be a solvent having a high drug solubility without any particular limitation, and include dichloromethane, ethyl acetate, acetone, ethanol, methanol, methyl ethyl ketone, methylene chloride, dichloroethane, chloroform, dioxane, dimethyl sulfoxide, acetonitrile, acetic acid, or the like.

According to the present invention, the drug may be dissolved in the organic solvent at a concentration of 0.001 to 10 g/mL. In addition, the organic solvent has a low boiling point in a solution in which the drug is dissolved, and is completely removed using a vacuum or rotary concentrator.

According to the present invention, the oil may include a paraffin oil, alpha-bisabolol, stearyl glycyrrhetinate, salicylic acid, tocopheryl acetate, panthenol, glyceryl stearate, cetyl octanolate, isopropyl myristate, 2-ethylene isopelagonate, di-$C_{12-13}$ alkyl malate, ceteatyl octanoate, butylene glycol dicaptylate/dicaprate, isononyl isostearate, isostearyl isostearate, cetyl octanoate, octyldodecyl myristate, cetyl esters, $C_{10-30}$ cholesterol/lanosterol ester, a hydrogenated castor oil, mono-glycerides, diglycerides, triglycerides, beeswax, canauba wax, suctose distearate, PEG-8 beeswax, candelilla (*euphorbia* cerifera) wax, a mineral oil, squalene, squalane, medium chain glyceride, myglyol, cremophor, a hydrogenated castor oil, a corn oil, a sesame oil, a cottonseed oil, glycerol, or the like.

According to the present invention, the oil may be mixed in a volume ratio of 5 to 20 to the organic solvent depending on solubility of the drug in the oil.

According to the present invention, the method for generating nanobubbles in a mixed liquid from which the organic solvent is removed or an oil containing a drug may utilize various methods existing in the relevant technical field, for example, a mechanical stirring method, an ultrasonic bubble generation method, a membrane passing-through method and a fluid circulation method. As an example, the nanobubble solution of the present invention may be prepared using an apparatus and method disclosed in Korean Patent Application No. 10-2019-0068228 entitled "An apparatus for generating a nanobubble Water".

According to the present invention, a type of a gas in the nanobubbles is not greatly limited, and may include an air, $CO_2$, $N_2$, $O_2$, $H_2$, Ar, perfluorobutane, perfluoropropane (octafluoropropane), etc.

According to the present invention, the aqueous solution containing the surfactant refers to a solution containing the surfactant in an aqueous solvent such as water, and a concentration thereof may range from 1 to 30 parts by weight based on 100 parts by weight of the total aqueous solution.

According to the present invention, the surfactant may include a cationic surfactant such as CTAB (cetyltrimethylammonium bromide), an anionic surfactant such as citrate, a non-ionic surfactant such as PVA (polyvinyl alcohol), a biopolymeric surfactant, and an amphoteric surfactant, without being limited to any type thereof.

For example, the cationic surfactant may be selected, without any limitation, from the group consisting of a quaternary ammonium compound, benzalkonium chloride, cetyltrimethylammonium bromide, chitosan, lauryldimethylbenzylammonium chloride, acyl carnitine hydrochloride, alkylpyridinium halide, cetyl pyridinium chloride, a cationic lipid, polymethylmethacrylate trimethylammonium bromide, a sulfonium compound, polyvinylpyrrolidone-2-dimethylaminoethyl methacrylate dimethyl sulfate, hexadecyltrimethyl ammonium bromide, a phosphonium compound, benzyl-di(2-chloroethyl)ethyl ammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride bromide, ($C_{12}$-$C_{15}$) dimethyl hydroxyethyl ammonium chloride, ($C_{12}$-$C_{15}$)dimethyl hydroxyethyl ammonium chloride bromide, coconut dimethyl hydroxyethyl ammonium chloride, coconut hydroxyethyl ammonium bromide, myristyl trimethyl ammonium methylsulfate, lauryl dimethyl benzyl ammonium chloride, lauryl dimethyl benzyl ammonium bromide, lauryl dimethyl(ethenoxy)4 ammonium chloride, lauryl dimethyl(ethenoxy)4 ammonium bromide, N-alkyl ($C_{12}$-$C_{18}$) dimethylbenzyl ammonium chloride, N-alkyl ($C_{14}$-$C_{18}$)dimethylbenzyl ammonium chloride, N-tetradecyldimethylbenzyl ammonium chloride monohydrate, dimethyl didecyl ammonium chloride, N-alkyl ($C_{12}$-$C_{14}$) dimethyl-1-naphthylmethyl ammonium chloride, trimethyl ammonium halide alkyl-trimethyl ammonium salt, dialkyl-dimethyl ammonium salt, lauryl trimethyl ammonium chloride, ethoxylated alkylamidoalkyldialkyl ammonium salt, ethoxylated trialkyl ammonium salt, dialkylbenzene dialkyl ammonium chloride, N-didecyldimethyl ammonium chloride, N-tetradecyldimethylbenzyl ammonium chloride monohydrate, N-alkyl ($C_{12}$-$C_{14}$) dimethyl-1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$ trimethyl ammonium bromide, $C_{15}$ trimethyl ammonium bromide, $C_{17}$ trimethyl ammonium bromide, dodecylbenzyl triethyl ammonium chloride, polydiallyldimethyl ammonium chloride, dimethyl ammonium chloride, alkyldimethyl ammonium halogenide, tricetyl methyl ammonium chloride, decyltrimethyl ammonium bromide, dodecyltriethyl ammonium bromide, tetradecyltrimethyl ammonium bromide, methyl trioctyl ammonium chloride, POLYQUAT 10, tetrabutyl ammonium bromide, benzyl trimethyl ammonium bromide, choline ester, benzalkonium chloride, stearalkonium chloride, cetyl pyridinium bromide, cetyl pyridinium chloride, a halide salt of quaternized polyoxyethylalkylamine, "MIRAPOL" (polyquaternium-2), "Alkaquat" (alkyl dimethyl benzyl ammonium chloride, prepared by Rhodia), an alkyl pyridinium salt, amine, an amine salt, an imide azolinium salt, protonated quaternary acrylamide, a methylated quaternary polymer, a cationic guar gum, benzalkonium chloride, dodecyl trimethyl ammonium bromide, triethanolamine, and poloxamin.

The anionic surfactants may be selected from the group consisting of ammonium lauryl sulfate, sodium 1-heptanesulfonate, sodium hexanesulfonate, sodium dodecylsulfate, triethanol ammonium dodecylbenzenesulfate, potassium laurate, triethanolamine stearate, lithium dodecylsulfate, sodium laurylsulfate, alkyl polyoxyethylene sulfate, sodium alginate, dioctyl sodium sulfosuccinate, phosphatidyl glycerol, phosphatidyl inositol, phosphatidylserine, phosphatidic acid and a salt thereof, glyceryl ester, sodium carboxymethylcellulose, bile acid and a salt thereof, cholic acid, deoxycholic acid, glycocholic acid, taurocholic acid, glycodeoxycholic acid, alkyl sulfonate, aryl sulfonate, alkyl phosphate, alkyl phosphonate, stearic acid and a salt thereof, palmitic acid and a salt thereof, calcium stearate, phosphate, sodium carboxymethylcellulose, dioctyl sulfosuccinate, dialkyl ester of sodium sulfosuccinic acid, phospholipid, and calcium carboxymethylcellulose, but are not limited thereto.

The non-ionic surfactant in the present specification may be selected from the group consisting of a Tween-based surfactant, a SPAN-based surfactant, polyoxyethylene fatty alcohol ether, polyoxyethylene sorbitan fatty acid ester, polyoxyethylene fatty acid ester, polyoxyethylene alkylether, a polyoxyethylene castor oil derivative, sorbitan ester, glyceryl ester, glycerol monostearate, polyethylene glycol, polypropylene glycol, polypropylene glycol ester, cetyl alcohol, cetostearyl alcohol, stearyl alcohol, arylalkyl polyether alcohol, a polyoxyethylene polyoxypropylene copolymer, poloxamer, poloxamine, methylcellulose, hydroxycellulose, hydroxymethylcellulose, hydroxyethylcellulose, hydroxypropylcellulose, hydroxypropylmethylcellulose, hydroxypropylmethylcellulose phthalate, an amorphous cellulose, a polysaccharide, a starch, a starch derivative, a hydroxyethyl starch, polyvinyl alcohol, triethanolamine stearate, amine oxide, dextran, glycerol, an acacia gum, cholesterol, tragacanth, and polyvinylpyrrolidone, but is not limited thereto.

The biopolymeric surfactant in the present specification may be selected from the group consisting of various polypeptides such as albumin, chitosan, heparin, polysaccharide, polyglycolic acid, polylactic acid, polyhydroxybutigic acid, a rubber, suberine, melanie, lignin and cellulose, a nucleic acid, and carbohydrate, but is not limited thereto.

The amphoteric surfactant in the present specification may be selected from the group consisting of N-dodecyl-N,N-dimethyl-3-ammonio-1-propanesulfonate, betaine, alkyl betaine, alkylamido betaine, amido propyl betaine, cocoamphocarboxyglycinate, sacosinate aminopropionate, aminoglycinate, imidazolinium betaine, an amphoteric midazoline, N-alkyl-N,N-dimethylammonio-1-propanesulfonate, 3-cholamido-1-propyldimethylammonio-1-propanesulfonate, dodecylphosphocholine, and sulfo-betain, but is not limited thereto.

Figure 1:
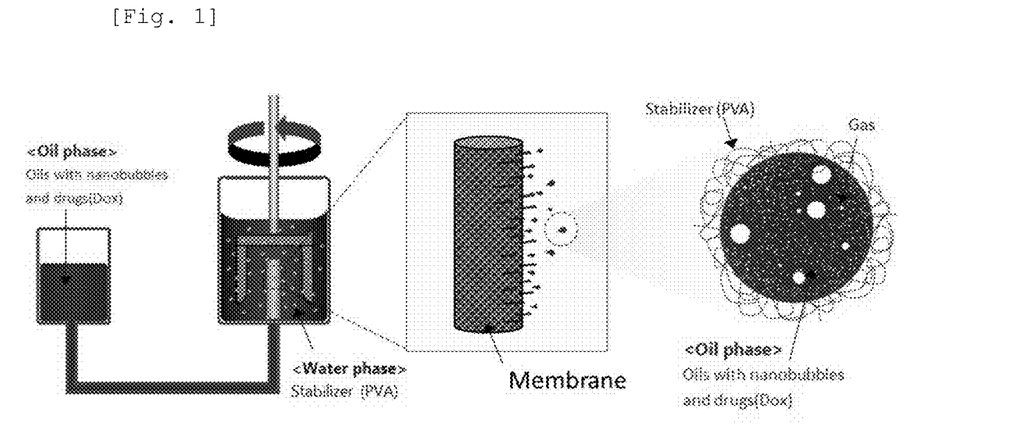
FIG. 1 is a diagram showing a process for preparing a microencapsulated drug delivery system by passing an oil containing a drug and nanobubbles according to the present invention through a porous membrane.

According to the present invention, in case the nanobubble solution is mixed with an aqueous solution containing the surfactant, the microcapsule particles of various sizes can be made using an emulsion generator as shown in FIG. 1. For example, in case the nanobubble solution containing a drug is mixed with the aqueous solution through a membrane (by automatically pushing it out using a pump built into the IMK-40 device), a pore size of the membrane may be 0.2 to 100 μm.

As another aspect for achieving the above purposes, the present invention provides a drug delivery system in which both the nanobubbles and the drug are encapsulated, the system being prepared according to the above method.

Figure 3:
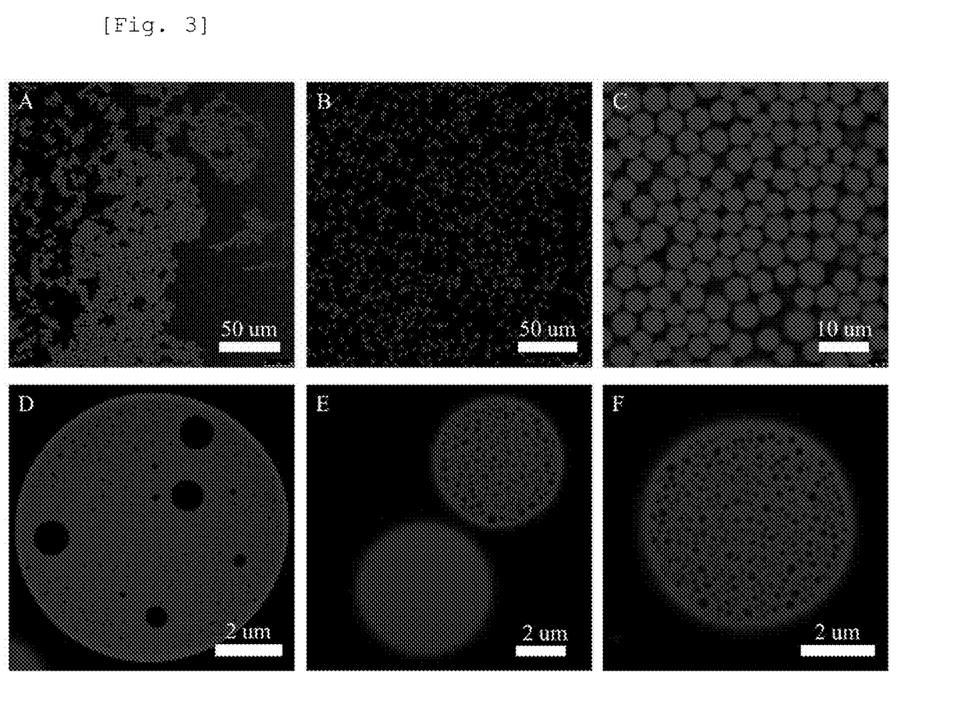
FIG. 3 is images of drug delivery systems in the form of microcapsules prepared according to the present invention. Specifically, A to C of FIG. 3 show fluorescent images of various concentrations in which the microcapsules having a uniform size are dispersed, wherein the red color is caused due to a fluorescence characteristic of the drug used (Nile red, doxorubicin). D to F of FIG. 3 shows appearances that each microcapsule is enlarged to contain nanobubbles therein. Specifically, E of FIG. 3 simultaneously shows microcapsules that the focus of a confocal analyzer matches and microcapsules that the focus does not match.
Figure 4:
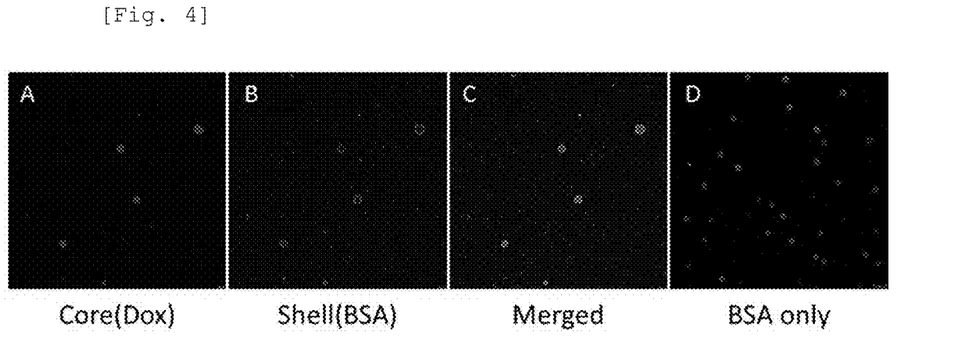
FIG. 4 shows fluorescent images of microcapsules prepared using albumin (Bovine serum albumin, BSA) to which a fluorescent pigment is fixed with a surfactant. Specifically.

The drug delivery system according to the present invention is prepared according to the above preparation method, and has an emulsion type in which the microcapsules containing a model drug (red, Nile red), nanobubbles (black within the microcapsule) and an oil are dispersed in an aqueous solution, as shown in FIG. 3.

According to the present invention, the microcapsule may have a size of about 0.3 to 20 μm, which varies with the pore size of the membrane used.

Figure 6:
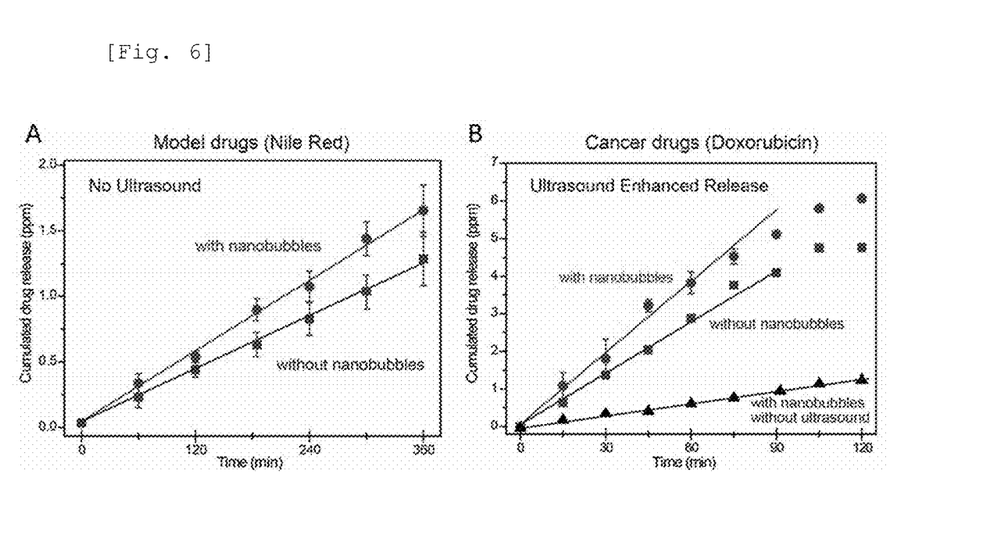
FIG. 6 shows skin permeability characteristics of drugs measured using a Franz cell and an artificial skin membrane. Specifically.
Figure 7:
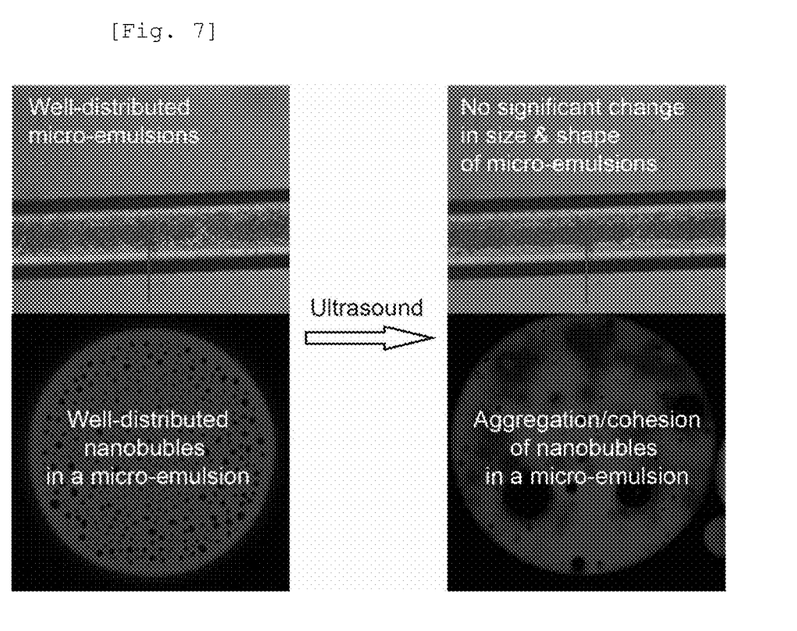
FIG. 7 is images showing characteristics generated when an ultrasound is irradiated to a drug delivery system in the form of microcapsules containing a drug and nanobubbles. Specifically, it can be confirmed that, when the microcapsules are irradiated with the ultrasound, there is no significant change in a size and a shape of each microcapsule, but sizes of the bubbles increase due to aggregation of the nanobubbles present inside each microcapsule.

According to the present invention, the drug delivery system maximizes a drug delivery efficiency by causing instantaneous high temperature and high pressure as the nanobubbles collapse or aggregate when an ultrasound is applied to the drug delivery system (FIGS. 6 and 7). Such ultrasound is not particularly limited and may include, for example, a focused ultrasound. In particular, by using the focused ultrasound, it is possible to effectively control release of the drug to a selected site of the human body from the outside.

As yet another aspect for achieving the above purposes, there is provided a cosmetic composition comprising the drug delivery system in the form of microcapsules in which both the drug and the nanobubbles are encapsulated.

The cosmetic composition comprising the drug delivery system may have effects such as skin whitening, skin elasticity improvement and wrinkle improvement, skin moisturizing, antioxidant, anti-inflammatory, etc., but is not limited thereto. Specifically, in case the drug delivery system of the present invention is used as the cosmetic composition, a drug contained in the drug delivery system may include active ingredients of (functional) cosmetics or cosmetically used active ingredients without limitation. The active ingredients of the cosmetics or the cosmetically used active ingredients are as described above.

The cosmetic composition according to the present invention may be prepared as a formulation selected from the group consisting of a solution, an external ointment, a cream, a foam, a nutrient lotion, an emollient lotion, a pack, a softening water, a milky lotion, a makeup base, an essence, a soap, a liquid cleaning agent, a bathing agent, a sunscreen cream, a sun oil, a suspension, an emulsion, a paste, a gel, a lotion, a powder, a soap, a surfactant-containing cleansing, an oil, a powder foundation, an emulsion foundation, a wax foundation, a patch, and a spray, but is not limited thereto.

Further, the cosmetic composition of the present invention may additionally include one or more of cosmetically acceptable carriers that are blended in common skin cosmetics, and may be appropriately blended with, for example, an oil, water, a surfactant, a moisturizer, a lower alcohol, a thickener, a chelating agent, a colorant, a preservative, a fragrance, and the like, as a conventional ingredient, but is not limited thereto.

Furthermore, as another aspect for achieving the above purposes, there is provided a contrast agent comprising the drug delivery system.

In the present invention, the term "contrast agent" refers to a formulation used to artificially make a difference in contrast and display it as an image so that a blood vessel or a tissue can be seen better for the purpose of determining a condition of the body organ and diagnosing a disease. More specifically, it may mean "an ultrasonic contrast agent". A typical example of the ultrasonic contrast agent may be the one using microbubbles or nanobubbles, and shows contrast characteristics due to a difference in an ultrasonic reactivity generated at the interface of microbubbles or nanobubbles injected into the body.

Since the drug delivery system of the present invention contains a plurality of nanobubbles within the microcapsules, it can be used not only as the drug delivery system, but also as the contrast agent. Further, the drug delivery system prepared according to the method of the present invention has characteristics that can perform both in vivo diagnosis and treatment at the same time, and the microcapsules containing a plurality of nanobubbles prepared without drugs have an excellent biocompatibility and an excellent stability in vivo. In addition, since the plurality of nanobubbles within one microcapsule can react with the ultrasound together, the drug delivery system can be used as an efficient ultrasonic contrast agent.

Further, if a contrast material such as an iodide contrast agent, a gadolinium contrast agent, a barium contrast agent, sulfahexafluoride, a fluorescent particle and a magnetic particle is contained together with the nanobubbles within the microcapsules, depending on the diagnostic method and purpose to be used, the drug delivery system can be used as the contrast agent having various characteristics. Embodiments to which the contrast agent can be applied may include X-ray imaging technology, Computer Tomography (CT), Magnetic Resonance Imaging (MRI), Positron Emission Tomography (PET), Nuclear imaging including ultrasonic image, etc., but are not particularly limited thereto.

As another aspect for achieving the above purposes, there is provided a method for delivering a drug, comprising the steps of administering, to an object, the drug delivery system in the form of a microcapsule in which both the drug and nanobubbles are encapsulated; and releasing the drug by irradiating an ultrasound to the administration site of the drug delivery system. The drug is as described above.

According to the present invention, the drug delivery system maximizes a drug delivery efficiency by causing instantaneous high temperature and high pressure as the nanobubbles collapse or aggregate when the ultrasound is applied to the drug delivery system. Specifically, a type of the ultrasound may be characterized by being a focused ultrasound, but is not particularly limited thereto. As an example, the method for delivering the drug according to the present invention utilizes a blood-brain barrier (BBB) disruption induced by irradiation of the ultrasound. In this case, when the drug delivery system is administered to the object and the ultrasound is irradiated to the administration site, the BBB disruption occurs instantaneously due to a hyperthermia caused by the ultrasound, which can increase drug permeability into a brain parenchyma.

The object may be a mammal including a mouse, a rat, a dog, a cat, a cattle, a horse, a pig, and a human, but is not particularly limited thereto. The administration of the drug delivery system may be performed by appropriately selecting the administration methods known to those skilled in the art in consideration of a type of the disease, an affected site, and a condition of the object.

As another aspect for achieving the above purposes, there is provided a method for treating a brain disease or a cancer, comprising the step of administering, to an object, the drug delivery system in the form of a microcapsule in which both a drug and nanobubbles are encapsulated; and releasing the drug by irradiating an ultrasound to an administration site of the drug delivery system.

The object and the administration are as described above. Specifically, the brain disease may be one or more selected from the group consisting of a thrombosis, an embolism, a stroke, a cerebral stroke, a cerebral infarction, a cerebral hemorrhage, a subarachnoid hemorrhage, and a brain tumor. The cancer may, for example, include a colon cancer, a pancreatic cancer, a gastric cancer, a liver cancer, a breast cancer, a cervical cancer, a thyroid cancer, a parathyroid cancer, a lung cancer, a non-small cell lung cancer, a prostate cancer, a gallbladder cancer, a biliary tract cancer, a non-Hodgkin's lymphoma, a Hodgkin's lymphoma, a blood cancer, a bladder cancer, a kidney cancer, an ovarian cancer, a melanoma, a colon cancer, a bone cancer, a skin cancer, a head cancer, an uterine cancer, a rectal cancer, a brain tumor, an anal muscle cancer, a fallopian tube carcinoma, an endometrial carcinoma, a vaginal cancer, a vulvar carcinoma, an esophageal cancer, a small intestine cancer, an endocrine adenocarcinoma, an adrenal cancer, a soft tissue sarcoma, an urethral cancer, a penile cancer, an ureter cancer, a kidney cell carcinoma, etc., but is not particularly limited thereto.

As another aspect for achieving the above purposes, there is provided a pharmaceutical composition for preventing or treating a brain disease or a cancer, comprising the drug delivery system in the form of a microcapsule in which both a drug and nanobubbles are encapsulated. The brain disease and the cancer are as described above.

In the present invention, the term "preventing" refers to any action that suppresses or delays the brain disease or the cancer by administrating the drug delivery system of the present invention, and the term "treating" refers to any action that improves or favorably changes the symptoms of the brain disease or the cancer by administrating the drug delivery system of the present invention.

The pharmaceutical composition of the present invention may further comprise a pharmaceutically acceptable carrier, an excipient or a diluent that is commonly used in the preparation of the pharmaceutical composition. The carrier may include a non-naturally occurring carrier. The pharmaceutical composition may be formulated in the form of an oral dosage such as a powder, a granule, a tablet, a capsule, a suspension, an emulsion, a syrup and an aerosol, an external preparation, a suppository, and s sterile injectable solution, respectively, according to a conventional method. The expression "pharmaceutically acceptable" means exhibiting the property that is not toxic to a cell or a human exposed to the composition. Specifically, the carrier may be used without being particularly limited as long as it is commonly used in the art and is pharmaceutically acceptable. Non-limiting examples of the carrier may include a saline solution, a sterile water, a Ringer's solution, a buffered saline solution, an albumin injection solution, a dextrose solution, a maltodextrin solution, glycerol, ethanol, and the like. They may be used alone or in combination of two or more. In addition, the pharmaceutical composition may be used by adding other conventional additives such as an antioxidant, a buffer solution and/or a bacteriostatic agent, if necessary, and may be formulated as a formulation for injection such as an aqueous solution, a suspension and an emulsion, a pill, a capsule, a granule or a tablet by additionally adding a diluent, a dispersant, a surfactant, a binder, a lubricant, and the like.

The pharmaceutical composition for preventing or treating the brain disease or the cancer according to the present invention may be administered in the manner commonly used in the art without being particularly limited. As a non-limiting example of the administration manner, the pharmaceutical composition may be administered orally or parenterally. In addition, the pharmaceutical composition for preventing or treating the brain disease or the cancer according to the present invention may be prepared in various formulations according to the intended administration manner.

Effect of the Invention

A drug delivery system using nanobubbles according to the present invention is prepared in the form of microcapsules in which both a drug and the nanobubbles are encapsulated, and, in particular, has an effect of maximizing a drug delivery efficiency as the nanobubbles collapse or aggregate when an ultrasound is applied to the drug delivery system.

Further, since a plurality of nanobubbles are contained in one microcapsule together, the prepared microcapsules can be utilized as an ultrasonic contrast agent.

Meanwhile, the effects described above are merely exemplary, and effects that are predicted or expected from the detailed constitutions of the present invention can also be added to the inherent effects of the present invention in terms of a person skilled in the art.

BRIEF DESCRIPTION OF THE DRAWINGS

FIG. 4A shows a red color because the drug (Doxorubicin) is contained within the microcapsule, FIG. 4B shows a green shell image showing albumin formed outside the microcapsule, and FIG. 4C is an image obtained by combining the images of FIGS. 4A and 4B. Further, FIG. 4D is a fluorescent image showing albumin present on a capsule surface by preparing a microcapsule containing no drug so as to clearly see the green color of albumin.

FIG. 5A shows a schematic diagram of the Franz cell used for analyzing the skin permeability, and FIG. 5B shows a schematic diagram for analyzing a drug release characteristic using an artificial skin/a human skin as the membrane.

FIG. 6A is a graph which shows a result of enhancing the skin permeability of a model drug (Nile Red) over time by pure nanobubbles without irradiating an ultrasound. FIG. 6B is a graph which compares the skin permeability for each of the case where the drug release is improved in a drug delivery system in the form of microcapsules containing a drug (Doxorubicin) and nanobubbles by irradiating the ultrasound, the case where the ultrasound is irradiated to the microcapsules containing no the nanobubbles, and the case where the microcapsules containing the nanobubbles are not irradiated with the ultrasound.

FIG. 8 shows results of observing a Doppler effect responding to irradiation of the ultrasound when a distilled water (A, E), an aqueous microcapsule solution without the nanobubbles (C, G), and an aqueous microcapsule solution containing the nanobubbles (B, D, F, H) are sequentially flowed into a rubber tube fixed between agarose gels.

DETAILED DESCRIPTION

Hereinafter, preferred embodiments of the present invention will be described with reference to the accompanying drawings. However, the embodiments of the present invention may be modified in various other forms, and the scope of the present invention is not limited to the embodiments as described below. Further, the embodiments of the present invention are provided in order to more completely explain the present invention to a person who has an average knowledge in the art.

Figure 2:
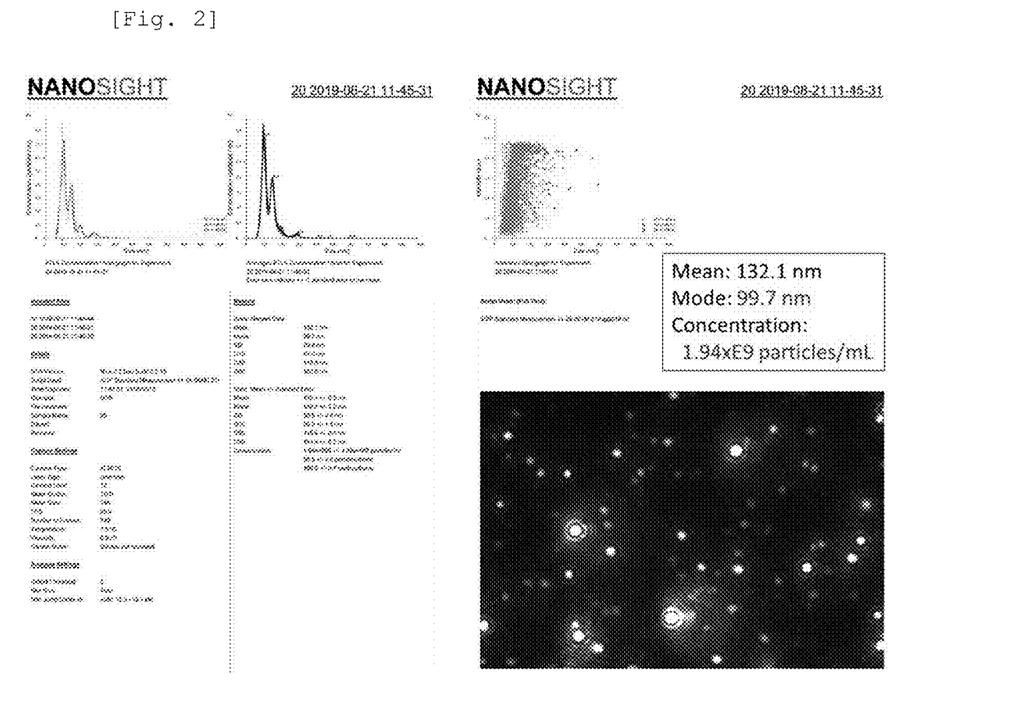
FIG. 2 is results obtained by measuring the number of bubbles within the nanobubble solution prepared according to the present invention, using an Nanoparticle Tracking Analyzer (NTA), and an image of nanobubbles.

Example: Preparation of a Drug Delivery System Dispersed in an Emulsion Form, in which Both a Drug and Nanobubbles are Encapsulated A model drug (Nile red) and a fat-soluble drug (Doxorubicin) of each 1 g were dissolved in dichloromethane of 100 mL, and then mixed with a corn oil of 1000 mL. Subsequently, the dichloromethane was removed completely using a rotary concentrator, and then a nanobubble solution was prepared using the "nanobubble water generator" of Korean Patent Application No. 10-2019-0068228 disclosed in the detailed description of the invention (see the container on the left in FIG. 1). The number of nanobubbles present in the prepared nanobubble solution was diluted in half and measured using a nanoparticle tracking analyzer (NTA). FIG. 2 shows that the nanobubbles of about 2 billion exist in the nanobubble solution of 1 mL.

The nanobubble solution prepared in this way was passed through a membrane having a pore size of "1 um" using an emulsion generator (IMK-40, MC Tech), and dispersed into an aqueous solution containing polyvinyl alcohol (PVA) or albumin as shown in FIG. 1 (see the right vessel of FIG. 1) to finally prepare an aqueous solution of a drug delivery system in the form of an emulsion.

As shown in FIG. 3, it was found that an oil containing nanobubbles and a fluorescent drug (Nile red or Doxorubicin) was encapsulated and prepared in the form of microcapsules using a confocal fluorescence analyzer, and a size of the microcapsule was around 5 um.

Figure 5:
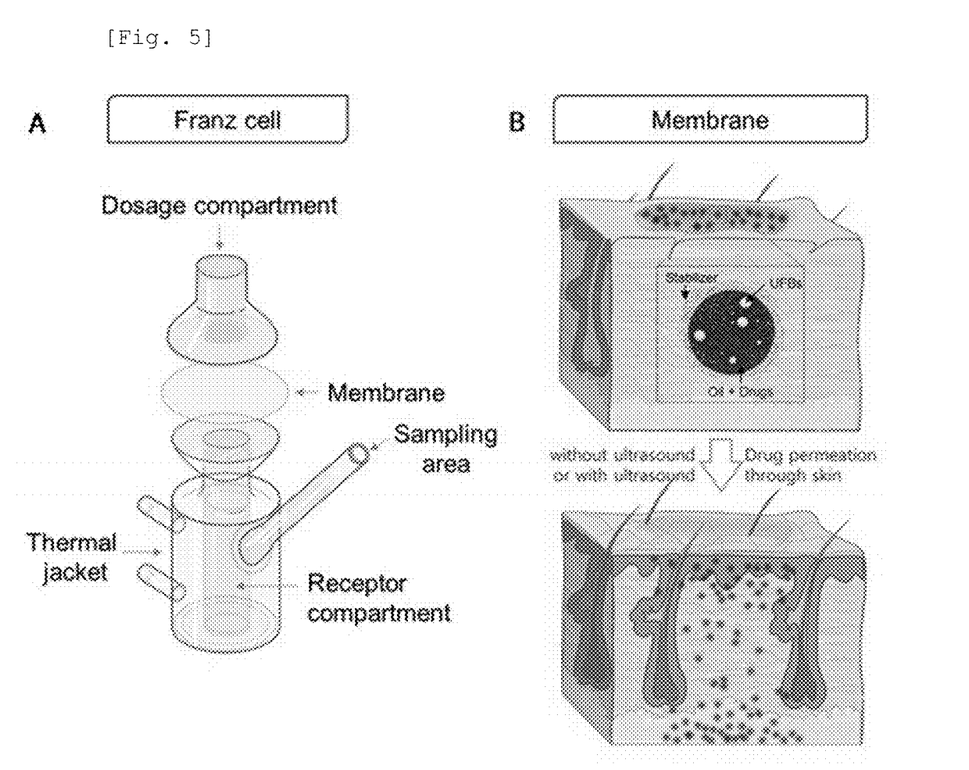
FIG. 5 shows a schematic diagram of a drug delivery through a Franz cell and a membrane used to measure a skin permeability characteristic. Specifically.

Experimental Example 1: Comparative Experiment of Drug Release According to Whether an Ultrasound is Irradiated or not A drug release characteristic of the prepared micro drug delivery system was measured by adding a solution in which the drug delivery system was dispersed in an upper portion (dosage compartment) of a Franz Cell in FIG. 5A. A solution used in a lower portion (Receptor compartment) of the Franz Cell was an aqueous DMSO solution of 20%. An amount of the drug delivered through a membrane was measured by circulating an aqueous solution having a constant temperature through a thermal jacket to maintain a temperature of the experimental device at 37° C., taking the sample at regular intervals through an sampling area and replenishing it with a pure solution. As a result, FIG. 6A showed that the microcapsule in which both the model drug (Nile Red) and the nanobubbles were microencapsulated improved a skin permeability of the drug compared to the microcapsule which did not contain the nanobubbles.

Additionally, an experiment for confirming enhancement of the drug release by irradiation of an ultrasound was conducted in an ultrasonic cleaner containing water of 1 L. As a result of comparing a rate of the drug release according to whether the ultrasound was irradiated or not, FIG. 6B showed that the microcapsule in which both the drug (Doxorubicin) and the nanobubbles were microencapsulated improved the skin permeability compared to the microcapsule which did not contain the nanobubbles, and also that the skin permeability of the microcapsule containing the nanobubbles was significantly deteriorated when the ultrasound was not irradiated.

Figure 8:
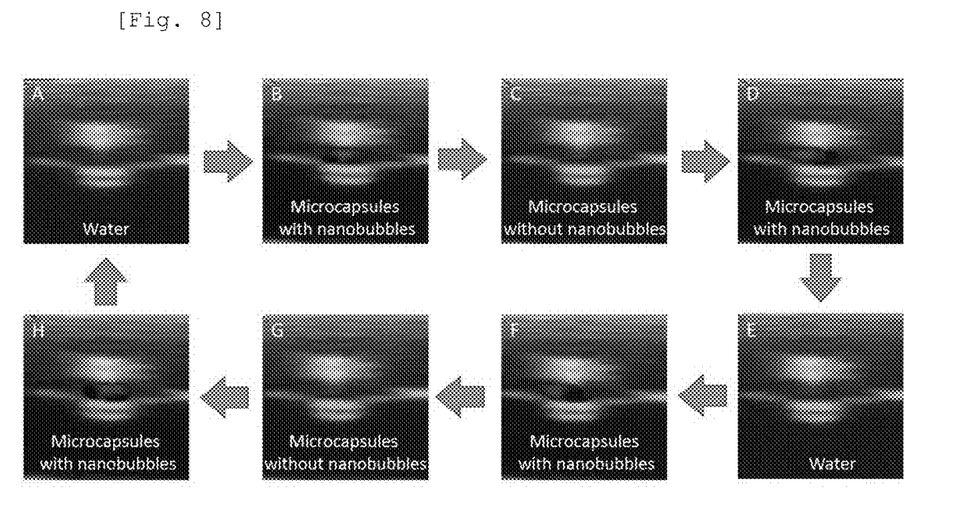
FIG. 8 is images showing ultrasonic contrast characteristics of the prepared microcapsules containing nanobubble. Specifically.

Experimental Example 2: Comparative Experiment of an Ultrasonic Contrast Characteristic of a Microcapsule Containing Nanobubbles In order to investigate an ultrasonic contrast characteristic of the nanobubble microcapsule prepared according to the method of the above Example, an agarose gel having a rubber tube fixed therein was prepared. Each of samples (a distilled water (A, E), an aqueous solution of the microcapsule without nanobubbles (C, G), and an aqueous solution of the microcapsule containing nanobubbles (B, D, F, H)) was taken with a syringe of 1 mL, and then, an ultrasonic probe (frequency of 11.43 MHz and power of 50 dB) was placed on the agarose gel and the sampled were imaged while each of the samples was flowed into the rubber tube fixed in the prepared agarose gel using a syringe pump (1 mL/min).

As a result, when the distilled water and the aqueous solution of the microcapsule without the nanobubbles were flowed, no special Doppler effect was observed even with irradiation of the ultrasound, but when the aqueous solution of the microcapsule containing the nanobubbles was flowed, a strong Doppler effect was observed, which confirmed the characteristic of the nanobubble microcapsules according to the present invention as the ultrasonic contrast agent.

It will be self-evident to a person who has an ordinary knowledge in the art that, although the present invention has been described in detail above, the scope of the present invention is not limited thereto, and various modifications and variations are possible without departing from the technical spirit of the present invention described in the claims.

What is claimed is:

1. A method for preparing a drug delivery system in the form of microcapsules in which both a drug and nanobubbles are microencapsulated, the method comprising the steps of:
    (a) dissolving the drug in an organic solvent, and then mixing it with an oil to prepare a mixed solution;
    (b) removing the organic solvent from the mixed solution;
    (c) preparing an oil solution containing both the drug and the nanobubbles, by generating the nanobubbles in the mixed solution from which the organic solvent has been removed; and
    (d) mixing the oil solution in an aqueous solution containing a surfactant,
    wherein the drug delivery system in the form of the microcapsules is prepared by encapsulating the drug together with the nanobubbles, both being contained in the oil,
    wherein the drug is a fat-soluble drug, and
    wherein the organic solvent is completely removed from the mixed solution using a vacuum or rotary concentrator.

2. The method according to claim 1, characterized in that the oil solution contains the nanobubbles having a diameter of 50 nm to less than 200 nm.

3. The method according to claim 1, characterized in that the drug delivery system is dispersed in an aqueous solution in the form of an emulsion.

4. The method according to claim 1, wherein the step (d) is to prepare the drug delivery system in the form of the microcapsules in which both the drug and the nanobubbles are encapsulated by passing the oil solution through a membrane in the aqueous solution containing the surfactant.

5. The method according to claim 1, characterized in that the drug is an active ingredient of cosmetics.

6. The method according to claim 1, characterized in that a concentration of the surfactant ranges from 2 to 30 parts by weight based on 100 parts by weight of the total aqueous solution.

\* \* \* \* \*